United States Patent [19]

Boltze et al.

[11] 4,410,536

[45] Oct. 18, 1983

[54] 7,8,9,10-TETRAHYDROTHIENO[3,2-e]PYRIDO[4,3-b]INDOLE COMPOUNDS AND THEIR ANTI-DEPRESSANT USE

[75] Inventors: Karl-Heinz Boltze, Bergisch-Gladbach; Peter-Rudolf Seidel, Cologne; Haireddin Jacobi, Leichlingen; Helmut H. Schwarz, Bergisch-Gladbach; Günter Schöllnhammer, Bergisch-Gladbach; Hans-Dieter Dell, Bergisch-Gladbach, all of Fed. Rep. of Germany

[73] Assignee: Troponwerke GmbH & Co. K.G., Cologne, Fed. Rep. of Germany

[21] Appl. No.: 258,174

[22] Filed: Apr. 27, 1981

Related U.S. Application Data

[63] Continuation of Ser. No. 97,094, Nov. 23, 1979, abandoned.

[30] Foreign Application Priority Data

Dec. 14, 1978 [DE] Fed. Rep. of Germany ....... 2854014

[51] Int. Cl.³ .................. C07D 471/22; A61K 31/44; A61K 31/495; A61K 31/54

[52] U.S. Cl. ...................................... 424/267; 544/60; 544/125; 544/361; 546/64; 424/246; 424/248.51; 424/250

[58] Field of Search .................. 546/64; 424/267, 246, 424/248.51, 250; 544/125, 60, 361

[56] References Cited

PUBLICATIONS

Forth et al., "Pharmacology & Toxicology," 1980, p. 455.
Janssen et al., Arzneimittelforschurng 17, 841 (1967).
"Handbook of Experimental Pharmacology", vol. 55, I, 1980, p. 400: Antipsychotics & Antidepressants.
Bergmann et al., Tetrahedron 32, 2847–52 (1976).

*Primary Examiner*—Mark L. Berch
*Attorney, Agent, or Firm*—Sprung, Horn, Kramer & Woods

[57] ABSTRACT

The present invention relates to certain new 7,8,9,10-tetrahydrothieno[3,2-e]pyrido[4,3-b]indole compound, to a process for their production and to their use as agents which have an influence on the central nervous system.

The ring system according to the invention has not hitherto been described in the literature.

24 Claims, No Drawings

7,8,9,10-TETRAHYDROTHIENO[3,2-E]PYRIDO[4,3-B]INDOLE COMPOUNDS AND THEIR ANTI-DEPRESSANT USE

This is a continuation of Application Ser. No. 097,094, filed Nov. 23, 1979 now abandoned.

According to the present invention we provide compounds which are 7,8,9,10-tetrahydrothieno[3,2-e]pyrido[4,3-b]indoles of the general formula

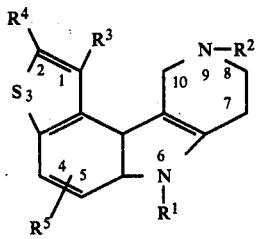

a quaternary salt thereof, or an acid or base addition salt thereof in which $R^1$, $R^2$ and $R^3$ are identical or different and each denotes a hydrogen atom, a straight-chain or branched alkyl, alkenyl or alkinyl group in which one $CH_2$ group is optionally replaced by an oxygen atom (to form an oxa-alkyl, oxa-alkenyl or oxa-alkinyl group) or an unsubstituted or lower alkyl-substituted nitrogen atom and in which one or more hydrogen atoms are optionally replaced by halogen or hydroxyl (to form an aza-alkyl, aza-alkenyl or aza-alkinyl group), denotes an aryl or aralkyl group, in which the aryl ring is optionally substituted by lower alkyl or alkoxy, halogen, hydroxyl or trifluoromethyl, denotes a cycloalkyl or cycloalkylalkyl group, in which the cycloalkyl radical is optionally substituted by lower alkyl or halogen, denotes an aryloxyalkyl group, in which the aryl radical is optionally substituted by lower alkyl or alkoxy, hydroxyl or halogen, denotes an aroylalkyl group, in which the aroyl group is optionally substituted by lower alkyl or alkoxy or by halogen atoms, denotes a heterocyclic or heterocycloalkyl group, in which the heterocyclic ring is optionally substituted by a lower alkyl group, an unsubstituted or substituted aryl group or an aralkyl group, denotes a carboxyl or optionally esterified carboxyl group, the ester radical being a straight-chain or branched alkyl group in which one hydrogen atom is optionally replaced by aryl, hydroxyl, alkoxy, amino or lower alkyl-amino or dialkylamino, denotes a carbamide grouping, in which the nitrogen atom is optionally substituted by lower alkyl groups, alkyl groups which carry basic substituents or heterocycloalkyl groups, or denotes a keto group, which is optionally substituted by alkyl, aryl or substituted aryl, $R^4$ denotes a hydrogen atom, a lower alkyl group, a substituted aryl group, a carboxyl group, a carboxyl group esterified by a lower alkyl or aralkyl, or an optionally substituted carbamide group and $R^5$ denotes a hydrogen or halogen atom, or a lower alkyl group or an alkoxy group.

According to present invention there is further provided a process for the production of compounds of the invention in which a hydrazine compounds of the formula

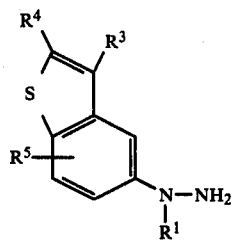

in which $R^1$, $R^3$, $R^4$ and $R^5$ have the meanings indicated above, is reacted with a piperidone of the formula

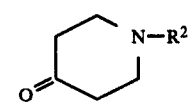

in which $R^2$ has the meaning indicated above, in the presence of an inert organic solvent at temperatures between 50° and 230° C. and optionally in the presence of a condensing agent, and, in the case where $R_1$ and $R_2$ in the compound of the formula (I) thus formed denote hydrogen atoms, the compound is, if desired, substituted by a radical mentioned above for $R_1$ and $R_2$ and, if desired, the free compound of the formula (I) is then converted into a quaternary salt or an addition salt. The quaternary salt is preferably formed with an alkyl halide, in which the alkyl group has, e.g. 1 to 12, preferably 1 to 4 carbon atoms and the halide is preferably chloride, bromide or fluoride; also included are the corresponding hydroxyalkyl halides.

As used herein and unless otherwise specified, the terms alkyl, alkenyl and alkinyl preferably contain up to 12 carbon atoms; the term aryl is preferably mono- or bi-cyclic carbocyclic aryl, such as phenyl, bisphenyl or naphthyl; the term aralkyl is preferably mono- or bi-cyclic carbocyclic aryl such as phenyl; biphenyl or naphthyl in the aryl portion and $C_1$–$C_4$ (preferably $C_1$–$C_2$) in the alkyl portion; the terms lower alkyl and lower alkoxy preferably contain 1 to 6, especially 1 to 4 carbon atoms; the term halogen is preferably fluorine, chlorine or bromine; the term cycloalkyl preferably contains 3 to 7, especially 5 to 6 ring members; the term cycloalkyl-alkyl preferably contains 3 to 7, especially 5 to 6 ring members in the cycloalkyl portion and 1 to 6, preferably 1 to 4 carbon atoms in the alkyl portion; the term aryloxyalkyl is preferably mono- or bi-cyclic carbocyclic aryl, such as phenyl, biphenyl or naphthyl in the aryl portion and contains up to 6, preferably up to 4 carbon atoms in the alkyl portion; the term heterocyclic preferably contains 4 to 7, especially 5 to 6 ring members and 1, 2 or 3 hetero atoms, such as oxygen, nitrogen or sulfur; and the term heterocycloalkyl preferably contains 4 to 7, especially 5 to 6 ring members and 1, 2 or 3 hetero atoms, such as oxygen, nitrogen or sulfur in the heterocyclic portion and 1 to 4, particularly 1 to 2 carbon atoms in the alkyl portion.

Surprisingly, the new compounds of the formula (I) according to the invention show pronounced and advantageous actions on the central nervous system and can be used, for example, an antidepressants in cases where antidepressants which are already known have undesired side-effects or habit-forming symptoms. They thus represent an advance in pharmacy.

Only some of the starting compounds of the general formula (II) and their precursors are known. They can be prepared by methods which are in themselves known, for example according to the following equation:

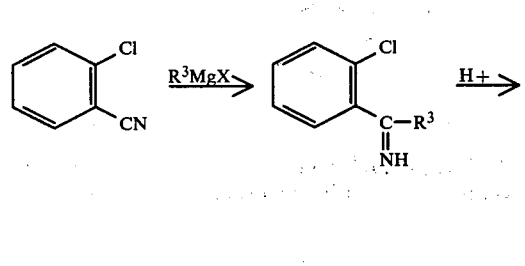

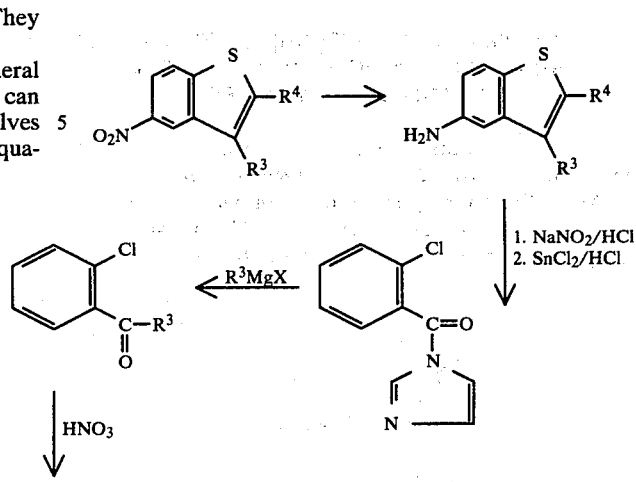

[compare: Org. Synth., Coll. volume III, 26,562 (1955)]

[compare: H.A. Staab inter alia Liebigs Ann. 655, 90 (1962)]

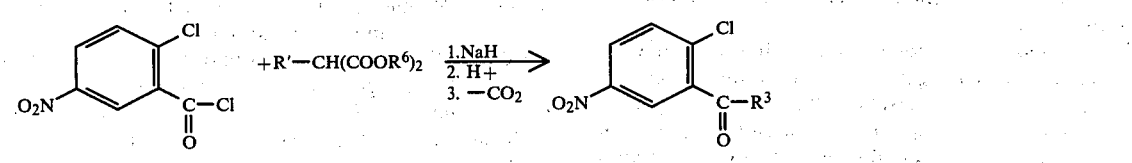

[compare: H. Henecka in Houben-Weyl volume 7/2b, page 1,338 et seq. (1976)]

($R'=R^3$ with the exception of $CH_2$ where this is possible amongst the substituents mentioned as $R^3$).

($R^6=H$; alkyl, preferably methyl or ethyl; tert.-butyl; tetrahydropyran-2-yl; or benzyl).

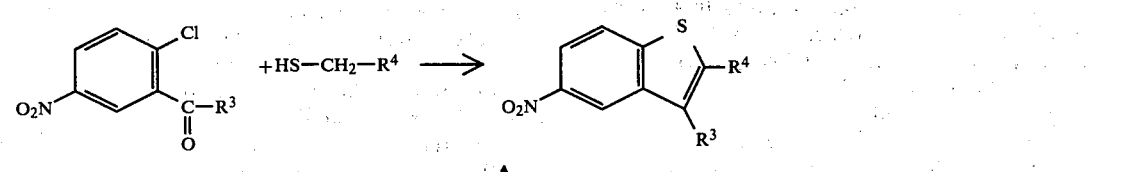

[Compare: S. Rossi and R. Trave Farmaco ED. Sci.15, 396 (1960) N.B. Chapman inter alia J. Chem. Soc. 1968. 518]

180° C./Cu
or
$Ac_2D—AcONa$

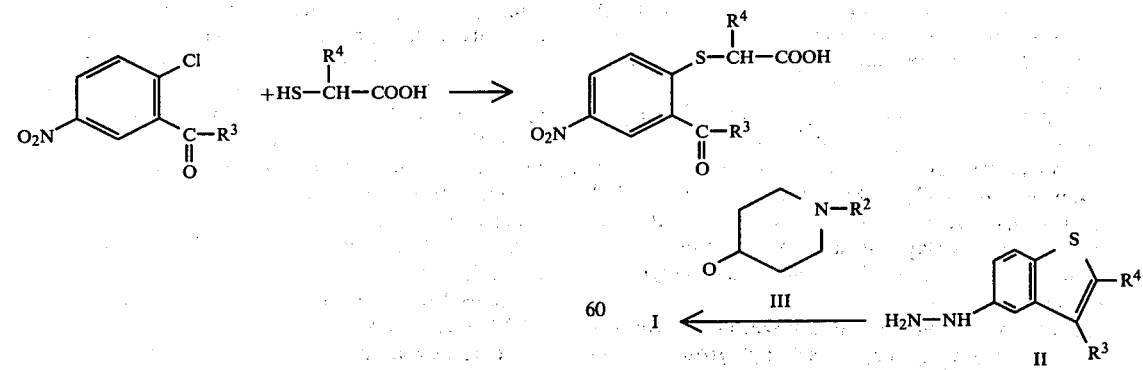

[compare: C. Angelini, Ann. Chim. (Rome) 47, 705 (1957) A. Ricci and N. Cagnoli, Ann. Chim. (Rome) 45, 172 (1955) S. Sauter and A. Dzerovicz, Monatsh. Chem. 101, 1,806 (1970)]

In the general formulae (I) and (II), an alkyl group $R^4$ preferably denotes methyl, ethyl, propyl, isopropyl, butyl, isobutyl, sec.-butyl, tert.-butyl or one of the various isomers of the pentyl group. The methyl group is particularly preferred.

An aryl group $R^4$ is preferably the phenyl group. It can be substituted by one or two methyl or ethyl groups, halogen atoms or methoxy groups.

An esterified carboxyl group $R^4$ is preferably an alkoxycarbonyl group with 1 to 3 carbon atoms in the alkyl part. The methoxy and ethoxy radical are particularly preferred. The aralkyl substituent is preferably the phenethyl group. If substituted, it is preferably substituted by one or two methyl or ethyl groups, halogen atoms, preferably chlorine or fluorine, or methoxy groups.

An aryloxycarbonyl group $R^4$ is preferably the benzyloxycarbonyl group.

An optionally substituted carbamide group $R^4$ is preferably an aminocarbonyl, methyl- or dimethyl-aminocarbonyl, ethyl- or diethyl-aminocarbonyl, phenylaminocarbonyl, benzylaminocarbonyl or cycloalkylaminocarbonyl group, the cycloalkyl ring containing 3 to 6 ring members.

In definition of $R^1$ and $R^3$ in the compounds of the formulae (I) and (II), and of $R^2$ in the compounds of the formulae (I) and (III) the straight-chain or branched, saturated or unsaturated alkyl group in which one chain member can be replaced by an oxygen atom or an unsubstituted or substituted nitrogen atom preferably denotes a grouping with up to 10 chain members. Specific examples which may be mentioned are: methyl, ethyl, propyl, isopropyl, butyl, isobutyl, pentyl, isopentyl, hexyl, 2-methoxyethyl, 2-ethoxyethyl, 3-methoxypropyl, tert.-butyl, allyl, dimethylaminoethyl, diethylaminoethyl, diethylaminopropyl, bromomethyl, chloromethyl and iodomethyl. Particularly preferred groupings are: methyl, propyl, isopropyl, isobutyl, butyl and dimethylaminoethyl.

An aryl group $R^1$, $R^2$ and/or $R^3$ is preferably the phenyl group. It is substituted preferably by one or two methyl, methoxy or hydroxyl groups, one trifluoromethyl group or one or two halogen, especially fluorine, atoms. Specific examples which may be mentioned are the phenyl, tolyl, trifluoromethylphenyl, fluorophenyl, methoxyphenyl and hydroxyphenyl group. The phenyl group is particularly preferred.

An aralkyl group $R^1$, $R^2$ and/or $R^3$ is preferably an aralkyl group with 7 to 16 carbon atoms. Specific examples which may be mentioned are: the benzyl, 2-phenylethyl and 1-phenylethyl group. The benzyl group and the 4,4-diphenylbutyl group are particularly preferred. Substituents which can be present are 1 to 2 methyl groups, methoxy groups or halogen atoms, fluorine atoms being particularly preferred.

A cycloalkyl or cycloalkylalkyl group $R^1$, $R^2$ and/or $R^3$ is preferably a cycloalkyl ring with 3 to 6 carbon atoms and an alkyl chain with 1 to 3 carbon atoms. Examples which may be mentioned are: cyclopropyl, cyclobutyl, cyclopentyl, cyclohexyl, cyclohexylmethyl and cyclohexylethyl.

An aryloxyalkyl radical $R^1$ to $R^3$ is preferably a phenyloxymethyl, phenyloxyethyl or phenyloxypropyl radical. The phenyl radical, if substituted, is preferably substituted by 1 to 2 methyl, methoxy or hydroxyl groups or by halogen atoms.

A heterocyclic group or heterocycloalkyl group $R^1$ $R^2$ and/or $R^3$ is preferably a heterocyclic group with 4 to 7 ring members, of which 1 to 3 can be hetero-atoms, whilst the alkyl part can contain 1 to 5 carbon atoms. Specific examples which may be mentioned are: piperidinoethyl, pyrrolidinopropyl, morpholinopropyl, thiomorpholinopropyl, morpholinobutyl, morpholinopentyl, piperazinoethyl, piperazinopropyl, piperazinobutyl and 4-piperidyl. The heterocyclic groups can be substituted by alkyl groups which contain 1 to 3 carbon atoms, or by benzyl groups or phenyl groups, it being possible for the latter to carry halogen atoms or methyl or methoxy groups as substituents.

An esterified carboxyl group $R^1$, $R^2$ and/or $R^3$ is, preferably a straight-chain or branched alkoxycarbonyl group with 1 to 6 carbon atoms, in which one hydrogen atom can be replaced by a phenyl radical or a dialkylamino group. Examples which may be mentioned are the methyl, ethyl, benzyl and 3-dimethylaminopropyl ester. The benzyl and 3-dimethylaminopropyl ester are particularly preferred.

An optionally substituted carbamide group $R^1$ to $R^3$ is preferably a carbamide group which is optionally substituted by alkyl groups with up to 6 carbon atoms and in which one hydrogen atom is optionally replaced by a basic radical. Specific examples which may be mentioned are: methylaminocarbonyl, dimethylaminocarbonyl, ethyl- and diethyl-aminocarbonyl, 3-dimethylaminopropylaminocarbonyl and 2-morpholinoethylaminocarbonyl.

A keto group $R^1$, $R^2$ and/or $R^3$ is preferably a keto group which is optionally substituted by an alkyl group with up to 6 carbon atoms or an aryl group. Examples of alkyl-substituted keto groups which may be mentioned are: the acetyl, propionyl, butyryl and valeryl group. The acetyl group is particularly preferred. An example of an aryl-substituted keto group which may be mentioned is the benzoyl group. It can in turn be substituted by 1 to 3 methyl, methoxy or trifluoromethyl groups or by halogen atoms.

In the case of the reaction according to the invention ((II)+(III)→(I)) it is possible, in principle, to differentiate between two different reaction conditions, depending on the reactivity of the reactants:

(1) In the case of reactant of formula (II) or (III) which are insensitive to acid, their salts, preferably the hydrochlorides, are employed, in a suitable inert diluent. Diluents which can be used are all the customary solvents suitable for the Fischer indole cyclisation.

(a): E. Enders in Houben-Weyl, volume 10/2, pages 546–586 (1967)

(b): A. Weissberger: The Chemistry of Heterocyclic Compounds. Indole Part I. Pages 232–317. Editor W. J. Houlihan, Wiley-Interscience 1972.

Examples of solvents which may be mentioned are: water, methanol, ethanol, propyl alcohol and, in particular, isopropyl alcohol, benzene, toluene, xylene or other organic solvents, such as, for example, dioxane, glacial acetic acid, polyphosphoric acid ethyl ester or high-boiling hydrocarbons. Condensing agents which can be used are all the customary catalysts suitable for the Fischer indole cyclisation (A. Weissberger: The Chemistry of Heterocyclic Compounds. Indole Part I, pages 246–258. Editor W. J. Houlihan, Wiley-Interscience 1972). Examples of condensing agents which may be mentioned are: zinc chloride, boron trifluoride, broron trifluoride etherate, hydrogen chloride, concentrated or anhydrous sulphuric acid, phosphoric acid polyphosphoric acid, polyphosphoric acid ethyl ester, formic acid, acid ion exchangers, for example "Amberlite" IR-120, or glacial acetic acid/hydrogen chloride.

In the case of more sensitive reactants of formula (II) and (III), the cyclisation reaction is appropriately carried out in the presence of an inert gas, for example nitrogen or argon. If necessary, hydrogen chloride can additionally be passed in as a condensing agent.

The reaction temperatures can be varied within a substantial range in the reaction of reactants of formulae (II) and (III). Preferably, the reaction is carried out between 50° and 150° C., more preferably between 70° and 120° C. The reaction times generally vary between ½ and 20 hours, preferably between 1 and 3 hours. The reaction is preferably carried out under normal pressure.

In carrying out the process according to the invention, the piperidone of the formula (III) is preferably employed in a slight excess of 0.1 to 0.5 mol per 1 mol of the hydrazine compound (II).

Working up is appropriately effected by evaporating the reaction solution, taking up the concentrate in a suitable inert organic solvent, rendering the mixture alkaline with a base, for example an alkali metal hydroxide or carbonate, such as NaOH or $NH_3$, and purifying the product, if appropriate with the aid of chromatography on $SiO_2$ or $Al_2O_3$.

It has sometimes proved appropriate to employ the corresponding ethylene-ketal instead of the ketone of formula (III).

(2) In the case of reactants of formula (II) or (III) which undergo condensation reactions less readily or which are distinguished, in particular, by their sensitivity to acids, the reaction is preferably carried out in high-boiling solvents. Examples of such solvents which may be mentioned are: dichlorobenzene, trichlorobenzene, ethylene glycol and ethylene glycol dimethyl ether, ethylene glycol being particularly preferred. The reaction temperatures can be varied within a substantial range. Preferably, the reaction is carried out between 150° and 230° C., more preferably between 180° and 210° C. and, at these temperatures, appropriately in the presence of inert gases. Working up is then effected as described for reaction conditions (I).

Compounds of the formula (I) in which $R^1$ and/or $R^2$ represents hydrogen can be appropriately substituted, for example by converting the NH compound into the sodium salt (a compound of formula (I) in which $R^1$=Na) with $NaNH_2$ or, preferably, NaH and reacting this salt with the correspondingly substituted halides, such as, for example, alkyl halides, in a manner which is in itself known.

The immediately above-mentioned reaction is preferably carried out in the presence of diluents. Possible diluents are all the inert organic solvents. Preferred solvents include aromatic hydrocarbons, such as, for example toluene, and higher ethers, such as ethylene glycol dimathyl ether and dioxane, but in particular aprotic solvents, such as, for example, dimethylformamide, hexamethylphosphoric acid triamide, N-methylpyrrolidone, dimethylacetamide and dimethylsulphoxide. The reaction times can be varied within a certain range. In general, heating to 40°-110° C., in particular to 60° to 80° C., for 2 to 6 hours is sufficient; in some cases room temperature is sufficient. Working up is then again effected in a manner analogous to that described above.

Thus, resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluenesulfonic, naphthalenesulfonic and sulfanilic acid; methionine, tryptophan, lysine and arginine.

In an analogous manner, a resulting acid compound can be converted into a corresponding addition salt by treatment with an amine, such as a mono-or di-alkyl or hydroxyalkyl amine, preferably having 1 to 8, particularly 1 to 4 carbon atoms in each alkyl portion.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Among the new 7,8,9,10-tetrahydrothieno[3,2-e]pyrido [4,3-b]indole salts of the invention those salts that are pharmaceutically acceptable are particularly important and are preferred.

The following 7,8,9,10-tetrahydrothieno[3,2-e]pyrido[4,3-b]indoles are new active compounds of particular interest: 9-methyl-, 9-benzyl-, 1-methyl, 1,9-dimethyl-, 1-methyl-9-propyl-, 9-benzyl-1-methyl-, 9-diethylaminoethyl-1-methyl-, 9-dimethylaminopropoxycarbonyl-1-methyl-, 9-methyl-1-phenyl-, 2-benzyloxycarbonyl-1-methyl-, 1,9-dimethyl-2-benzyloxycarbonyl, 1-butyl-9-methyl-, 9-sec.-butyl-, 9-sec.-butyl-1-methyl, 9-isopropyl-, 9-isopropyl-1-methyl-, 1-butyl-, 1-butyl-9-isopropyl-, 9-propyl-, 1-butyl-9-benzyl-, 1-phenyl-, 9-sec.-butyl-1-phenyl-, 9-benzyl-1-phenyl-, 9-[4-(4-fluorophenyl)-4-oxobutyl]-1-methyl-, 9-[4,4-bis-(4-fluorophenyl)butyl]-1-methyl-, 9-(3-dimethylaminopropyl)-1-methyl-, 6-propyl-, 9-methyl-1-phenyl-6-propyl-, 6,9-dibenzyl-1-methyl-, 6-(3-dimethylaminopropyl)-1,9-dimethyl-, 9-benzyl-6-(3-dimethylaminopropyl)-1-methyl-, 6-(3-dimethylaminopropyl-1-methyl-, 9-ethyl-, 6-ethyl-9-methyl-, 6-isobutyl-9-methyl-, 6-allyl-9-methyl-, 6-isopentyl-9-methyl-, 6-cyclohexylmethyl-9-methyl-, 6-ethyl-9-isopentyl-, 6-hexyl-9-isopentyl-, 6-phenyl-9-methyl-, 1-methyl-9-ethyl-, 1-methyl-9-butyl-, 1-methyl-9-cyclohexyl-methyl-, 1-methyl-9-cyclohexyl-, 1-methyl-9-phenyl-, 1-methyl-9-tert.-butyl-, 1-methyl-9-isopentyl-, 1-methyl-9-(2-methoxyethyl)-, 1-methyl-9-(2-phenoxyethyl)-, 1-methyl-9-(3-phenylpropyl)-, 1-methyl-9-benzyhydryl-, 1,6,9-trimethyl-, 1,9-dimethyl-6-ethyl-, 1,9-dimethyl-6-(2-butyl)-, 1,9-dimethyl-6-isopropyl-, 1,9-dimethyl-6-hexyl-, 1,9-dimethyl-6-butyl-, 1,9-dimethyl-6-(2-methoxyphenyl)-, 1,9-dimethyl-6-benzhydryl-, 1,9-dimethyl-6-cinnamyl-, 1,9-dimethyl-6-(4-fluorophenyl)-4-oxobutyl)-, 1,9-dimethyl-6-(3-dimethylamino-2-methylpropyl)-, 1-methyl-6,9-bis(2-ethoxyethyl)-, 1-methyl-6-phenethyl-9-(2-(2-dimethylaminoethoxy)ethyl)-, 1-methyl-6,9-bis(-cyclohexylmethyl)-, 1-methyl-6-ethyl-9-(4-methyl-1-piperazinylacetyl)-, 1-methyl-6-ethyl-9-(1-methyl-4-piperidylcarbonyl)-, 1,6-dimethyl-9-(1-(4-fluorophenyl)-4-piperidylcarbonyl)-, 1,9-dimethyl-6-phenyl-, 1,9-dimethyl-6-(4-fluorophenyl)-, 1-ethyl-, 1-ethyl-9-methyl-, 1,9-diethyl-, 1-ethyl-9-isopropyl-, 1-ethyl-9-propyl-, 1-ethyl-9-isobutyl-, 1-ethyl-9-allyl-, 1-ethyl-9-cyclohexyl-, 1-ethyl-9-phenyl-, 1-ethyl-9-(2-ethoxyethyl)-, 1-ethyl-9-(3-dimethylaminopropyl)-, 1-ethyl-6,9-dimethyl-, 1-ethyl-6-(2-methoxyethyl)-9-methyl-, 1-ethyl-6-acetyl-9-methyl-, 1-ethyl-6-(2-phenoxyethyl)9-methyl-, 1-ethyl-6-(4-chlorobenzyl)-9-methyl-, 1-ethyl-6-(3-dimethylaminopropyl)-9-methyl-, 1,6-diethyl-9-benzhydryl-, 1-ethyl-6-(3-dimethylamino-2-methylpropyl)9-benzhydryl-, 1-ethyl-6-(2-ethoxyethyl)-9-benzhydryl-, 1-butyl-9-ethyl-, 1-butyl-9-propyl-, 1-butyl-9-cyclohexyl-, 1-butyl-9-benzhydryl-, 1-butyl-6,9-dimethyl-, 1-butyl-6-isopropyl-9-methyl-, 1-butyl-6-allyl-9-methyl-, 1-butyl-6-(2-ethoxyethyl)-9-methyl-, 1-butyl-6-(3-dimethylamino-2-propyl)-9-methyl-, 1-butyl-6-(3-dimethylamino-2-methylpropyl)-9-methyl-, 1-butyl-6-(2-phenethyl)-9-ethyl-, 1-butyl-6-benzhydryl-9-ethyl-, 1-butyl-6-(3-phenylpropyl)-9-ethyl-, 1-butyl-6-(4-chlorobenzyl)-9-ethyl-, 1-butyl-6-(2-methoxyethyl)-9-ethyl-, 1-isopentyl-, 1-isopentyl-9-methyl-, 1-isopentyl-9-ethyl-, 1-isopentyl-9-isopropyl-, 1-isopentyl-9-allyl-, 1-isopentyl-9-cyclohexyl-, 1-isopentyl-9-phenyl-, 1-isopentyl-9-(1-methyl-4-piperidylcarbonyl)-, 1-isopentyl-6,9-dimethyl-, 1-isopentyl-6-(2-methoxyethyl)-9-methyl-, 1-isopentyl-6-(3-dimethylaminopropyl)-9-methyl-, 1-isopentyl-6-cinnamyl-9-methyl-, 1-isopentyl-6-(2-phenoxyethyl)-9-(3-dimethylaminopropyl)-, 1-isopentyl-6-cyclohexylmethyl-9-(3-dimethylaminopropyl)-, 1-(2-cyclohexylethyl)-, 1,2-cyclohexylethyl)-9-methyl-, 1-(2-cyclohexylethyl)-9-methyl-, 1-(2-cyclohexylethyl)-9-ethyl-, 1-(2-cyclohexylethyl)9-isopropyl-, 1-(2-cyclohexyethyl)-9-allyl-, 1-(2-cyclohexylethyl)-9-cyclohexyl-, 1-(2-cyclohexylethyl)-9-(1-methyl-4-piperidylcarbonyl)-, 1-(2-cyclohexylethyl)-6,9-dimethyl-, 1-(2-cyclohexylethyl)-6-phenyl-9-methyl-, 1-(2-cyclohexylethyl)-9-(3-(4-methyl-1-piperazinyl)-propyl)-, 1-phenyl-9-ethyl-, 1-phenyl-9-propyl-, 1-phenyl-9-isopropyl-, 1-phenyl-9-allyl-, 1-phenyl-9-(2-phenethyl)-, 1-phenyl-9-(2-ethoxyethyl)-, 1-phenyl-9-(4-fluorophenyl)-4-oxobutyl)-, 1-phenyl-6-propyl-9-methyl-, 1-phenyl-6-isopentyl-9-methyl-, 1-phenyl-6-cyclohexylmethyl-9-methyl-, 1-phenyl-6-benzhydryl-9-methyl-, 1-phenyl-6-(2-methoxyethyl)-9-methyl-, 1-phenyl-6-(3-dimethylaminopropyl)-9-methyl-, 1-phenyl-6-(3-phenylpropyl)-9-methyl-, 1-(2-phenethyl)-, 1-(2phenethyl)-9-allyl-, 1-(2-phenethyl)-9-propyl-, 1-(2-phenethyl)-9-cyclohexyl-, 1-(2-phenethyl)-9-(2-ethoxyethyl)-, 1-(2-phenethyl)9-(1-methyl-4-piperidylcarbonyl)-, 1-(2-phenethyl)-6,9-dimethyl-, 1-(2-phenethyl)-6-(2-methoxyethyl)-9-methyl-, 1-(2-phenethyl)-6-cyclohexylmethyl-9-methyl, 1-(2-phenethyl)-6-(3-dimethylaminopropyl)-9-methyl-, 1-(2-phenethyl)-6-(4-bromobenzyl)-9-(2-(2-dimethylaminoethoxy)ethyl-, 1-(2-phenethyl)-6-isobutyl-9-(2-(2-dimethylaminoethyl)ethyl)-, 2,9-dimethyl-, 2-methyl-9-ethyl-, 2-methyl-9-cyclohexyl-, 2,6,9-trimethyl-, 2,9-dimethyl-6-(4-fluorobenzyl)-, 2,9-dimethyl-6-allyl-, 2-methyl-6-isopentyl-9-(1-methyl-4-piperidylcarbonyl)-, 1,2-dimethyl-, 1,2,9-trimethyl-, 1,2-dimethyl-9-allyl-, 1,2,6,9-tetramethyl-, 1,2,9-trimethyl-6-benzhydryl-, 1,2,9-trimethyl-6-(2-ethoxyethyl)-, 1,2-diphenyl-, 1,2-diphenyl-9-methyl-, 1,2-diphenyl-6,9-dimethyl-, 1,2-diphenyl-6-(3dimethylaminopropyl)-9-methyl-, 1-methyl-2-phenyl-, 1,9-dimethyl-2-diphenyl-, 1-methyl-2-phenyl-9-isobutyl-, 1-methyl-2-phenyl-6-ethyl-9-isobutyl-, 1-methyl-2-phenyl-6-ethyl-9-(3-dimethylaminopropyl)-, 1-methyl-2-phenyl-6-(2-ethoxyethyl)-9-methyl-, 1-ethyl-2-phenyl-9-methyl-, 1-ethyl-2-phenyl-9-cyclohexyl-, 1-ethyl-2-phenyl-6,9-bis(cyclohexylmethyl)-, 1-ethyl-6-cyclohexylmethyl-9-methyl-, 2-phenyl-9-methyl-, 2-phenyl-6-(3-dimethylaminopropyl)-9-methyl- and,in addition, 6,9-bis(3-dimethylaminopropyl-1-methyl-7,8,9,10-tetrahydrothieno[3,2-e]pyrido[4,3-b]indole and 1,9-dimethyl-7,8,9,10-tetrahydrothieno[3,2-e]pyrido[4,3-b]indole methiodide.

Particularly preferred compounds of the present invention are those in which $R^1$ denotes a hydrogen atom or a straight-chain or branched alkyl group with 1 to 4 carbon atoms which is optionally substituted by alkoxy with 1 or 2 carbon atoms or by alkylamino or dialkylamino with in each case 1 or 2 carbon atoms per alkyl radical, denotes an aralkyl radical, preferably a benzyl radical, the phenyl radical thereof optionally being substituted by halogen, preferably by chlorine or fluorine, or denotes an aryl radical, preferably a phenyl radical, the aryl radical optionally being substituted by alkyl or alkoxy with 1 or 2 carbon atoms or optionally being substituted by halogen, preferably by fluorine or chlorine, or by hydroxyl or trifluoromethyl.

$R^2$ denotes a hydrogen atom or a straight-chain or branched or cyclic alkyl group with up to 6 carbon atoms, this alkyl group optionally being substituted by alkoxy with 1 or 2 carbon atoms or by alkylamino or dialkylamino with in each case 1 or 2 carbon atoms in the alkyl part, denotes an aryl radical, preferably a phenyl radical, this aryl radical optionally being substituted by alkyl with 1 or 2 carbon atoms or by alkoxy with 1 or 2 carbon atoms or by halogen or trifluoromethyl, denotes an aralkyl radical, preferably a benzyl or phenethyl radical, the phenyl ring thereof optionally being substituted by halogen, preferably chlorine or fluorine, denotes an alkenyl radical with up to 4 carbon atoms, denotes an alkoxycarbonyl radical with up to 4 carbon atoms in the alkoxy radical, this alkoxy radical optionally being substituted by dialkylamino groups with in each case 1 or 2 carbon atoms in the alkyl group, denotes a phenyloxoalkyl radical, the alkyl radical thereof containing up to 4 carbon atoms and the phenyl radical thereof being substituted by halogen, preferably by fluorine or chlorine, the phenyloxoalkylradical most preferably being a 4-(4-fluorophenyl)-4-oxobutyl radical, or denotes a biphenylalkyl radical with 1 to 4 carbon atoms in the alkyl radical, the phenyl radical thereof optionally being substituted by halogen, preferably by fluorine or chlorine, the biphenylalkyl radical most preferably being a 4,4-bis-fluorophenyl-butyl radical, $R^3$ denotes a hydrogen atom or a straight-chain or branched alkyl group with 1 to 6 carbon atoms which is optionally substituted by halogen, preferably by fluorine or chlorine, or denotes a phenyl radical which is optionally substituted by halogen, preferably fluorine or chlorine, or trifluoromethyl, $R^4$ denotes a hydrogen atom, an alkyl group with 1 to 4 carbon atoms, preferably with 1 or 2 carbon atoms, or a benzyloxycarbonyl group, and $R^5$ denotes a hydrogen atom.

Especially preferred compounds of the present invention are those in which $R^1$ denotes a hydrogen atom or a straight-chain or branched alkyl group with 1 to 4 carbon atoms, which is optionally substituted by alkoxy with 1 or 2 carbon atoms, or denotes a phenyl radical, $R^2$ denotes a hydrogen atom, a straight-chain or branched or cyclic alkyl group with up to 6 carbon atoms or a phenyl or a benzyl radical, $R^3$ denotes a hydrogen atom, an alkyl group with 1 or 2 carbon atoms or an aralkyl radical, preferably a benzyl or phenethyl radical, $R^4$ denotes a hydrogen atom or an alkyl group with 1 or 2 carbon atoms and $R^5$ denotes a hydrogen atom.

As stated above, the invention also relates to the use in medicine of the compounds of the invention.

The present invention provides pharmaceutical compositions containing as active ingredient a compound of the invention in admixture with a solid, liquid or liquefied gaseous diluent.

The invention further provides pharmaceutical compositions containing as active ingredient a compound of the invention in the form or a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agaragar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycoles and fats (e.g. cocoa oil and high esters[e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-ager and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 to 500 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned conditions in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitroneally, subcutaneously and intravenously) or rectally, preferably orally or intravenously. Preferred pharmaceutical compositions and medicaments are therefore those adapted for administration such as oral or intravenous administration. Administration in the method of the invention is preferably oral or intravenous administration.

In general it has proved advantageous in medicine to administer amounts of from 0.05 mg to 100 mg/kg, preferably 0.1 mg to 10 mg/kg, of body weight per day, optionally in the form of several individual administrations, to achieve effecti e results. An individual administration preferably contains the active compound or compounds according to the invention in amounts of 0.016 mg to 33.3 mg/kg, preferably 0.03 mg to 3.33 mg/kg, of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples A to G illustrate the production of novel starting materials and Examples 1 to 61 illustrate the protection of compounds of the present invention.

EXAMPLE A

3-Butyl-5-hydrazinobenzothiophene hydrochloride 12.1 g of 3-butyl-5-aminobenzothiophene hydrochloride are mixed with 50 ml of $H_2O$ and 50 ml of concentrated HCl, and a solution of 3.6 g of $NaNO_2$ in 40 ml of water is added dropwise at $-5°$. The solution obtained is added dropwise to a mixture, cooled to $-15°$ C., of 28.4 g of $S_2Cl_2.2H_2O$ and 50 ml of concentrated HCl. After warming the reaction mixture to room temperature, the precipitate which has separated out is filtered off, washed with cold concentrated HCl and put into ice-water and the mixture is covered with a layer of ether and rendered alkaline with 20% strength NaOH. The ethereal phase is washed and dried and acidified with HCl/ether; the precipitate is boiled up in ethyl acetate and filtered off. Melting point: 168°–170° C.

Yield: 10.0 g (78% of theory)

EXAMPLE 8

3-Butyl-5-aminobenzothiophene hydrochloride 38 g of the corresponding 5-nitro compound are hydrogenated in 1.2 liters of ethyl acetate on 13 g of Pd/C at room temperature (0.5 hour). The Pd/C is then filtered off, the filtrate is acidified with HCl/ether and the precipitate which has separated cut is filtered off at 20° C. and boiled up in ethyl acetate. Melting point: 182°–183° C.

Yield: 74 g (95% of theory)

EXAMPLE C 3-butyl-5-nitro-benzothiophene 5.6 g of Cu are heated to 210° C. under $N_2$ for 20 minutes and, after cooling, 110 g of quinoline and 27.9 g of 3-butyl-5-nitro-2-benzothiophenecarboxylic acid are added. The mixture is heated to 180° C., whilst stirring, until the evolution of $CO_2$ has ended. After cooling, the reaction mass is decanted off with $CH_2Cl_2$, the quinoline is washed out by shaking with 20% strength HCl and the organic phase is washed, dried and purified on $Al_2O_3$. Melting point: 82°–83° C.

Yield: 21.7 g (92% of theory)

EXAMPLE D

3-Butyl-5-nitro-2-benzothiophenecarboxylic acid 107 g of the corresponding ethyl ester are added to 31.7 g of NaOH, dissolved in 360 ml of 50% strength ethanol, and the mixture is boiled for 2 hours. After evaporation, the residue is taken up in water and the mixture is acidified. Melting point: 238°–240° C.

Yield: 100.6 g (98% of theory)

EXAMPLE E

3-Butyl-5-nitro-2-benzothiophenecarboxylic acid ethyl ester 12 g of Na are dissolved in 250 ml of ethanol; 62.5 g or mercaptoacetic acid ethyl ester and a solution of 132.5 g of 2-chloro-5-nitrovalerophenone in 680 ml of ethanol are successively added dropwise to this Na-ethylate solution at 20° C. After boiling the mixture for 3 hours and leaving it to stand at 8° C. for a prolonged period, the precipitate which are separated out is filtered off and taken up in chloroform and the chloroform mixture is washed and dried. After evaporating off the solvent, the product is recrystallised from ethanol. Melting point: 92°–93° C.

Yield: 90 g (56% of theory)

EXAMPLE F

2-Chloro-5-nitrovalerophenone 133 g of 2-chlorovalerophenone are added dropwise to 715 ml of fuming $HNO_3$ at $-15°$ C. and the mixture is poured onto 4 kg of ice. The aqueous phase is then extracted with chloroform and the organic phase is washed, dried and concentrated. The oily compound is further processed as the crude product.

Yield: 150 g (92% of theory)

EXAMPLE G

2-Chlorovalerophenone 68.8 g of 2-chlorobenzonitrile in 800 ml of ether are added dropwise to an ethereal mixture of butyl-MrBr (contained from 205.5 g of butyl bromide and 26.5 g of Mg filings). The mixture is boiled for 10 hours and 600 ml of approximately 20% strength HCl are then added dropwise. After adding 600 ml of water, the ethereal phase is washed, dried and evaporated and the residue is distilled. Boiling point: 138°–140° C.

$n_D^{20}$: 1.5203. Yield: 84 g (85% of theory)

The hydrazinobenzothiophene derivatives below were prepared analogously to the 3-butyl-5-hydrazinobenzothiophene hydrochloride described, from the corresponding 5-aminobenzothiophene hydrochlorides: 5-hydrazino- (base melting point: 180°–188° (decomposition), hydrochloride melting point: 214°), 3-methyl-5-hydrazino- (base melting point: 83°–87°, hydrochloride melting point: 177°), 3-ethyl-5-hydrazino- (base melting point 35°–37°, hydrochloride melting point: 188°–190°), 3-isopentyl-5-hydrazino- (hydrochloride melting point: 172°–174° C.), 3-phenethyl-5-hydrazinothydrochloride melting point: 181°–185° (decomposition)), 3-cyclohexylethyl-5-hydrazino-, 2-benzyloxycarbonyl-3-methyl-5-hydrazine- (base melting point 113°, hydrochloride melting point: 192° (decomposition)), 3-phenyl-5-hydrazino- (base melting point: 142°–143°, hydrochloride melting point: 174° (decomposition)), 2-methyl-5-hydrazino-, 1,2-dimethyl-5-hydrazino-, 2-phenyl-5-hydrazino- and 1,2-diphenyl-5-hydrazino-benzothiophene hydrochloride.

EXAMPLE 1

7.8,9,10-Tetrahydrothieno[3.2-e]pyrido[4,3-b]indole 15 g of 5-hydrazinobenzothiophene hydrochloride and 15 g of 4-piperidone are boiled in 450 ml of isopropanol under a reflux condenser for 2 hours. After cooling the mixture, the precipitate which has separated out is filtered off and suspended in 2 N NaOH. A layer of methylene chloride is introduced under the suspension and the mixture is stirred; the layers are then separated and the organic phase is washed, dried and evaporated. After recrystallisation of the residue from isopropanol, 7,8,9,10-tetrahydrothieno[3,2-e]pyrido[4,3-b]indole of melting point 190° is obtained.

Yield: 13 g (76% of theory)

$C_{13}H_{12}N_2S$ (228.321): Calculated: C 68.39%, H 5.30%, N 12.27%, S 14.04%. Found: C 68.54%, H 5.32%, N 12.17%, S 14.07%.

Melting point of the lactate: 210°220° C. (decomposition).

EXAMPLE 2

9-Methyl-7,8,9,10-tetrahydrothieno[3,2-e]pyrido[4,3-b]indole 4 g of 5-hydrazinobenzothiophene hydrochloride, suspended in 100 ml of isopropanol, are combined with 2.8 ml of 1-methyl-4-piperidone hydrochloride under $N_2$. The solution is brought to the boil and 10 ml of isopropanol saturated with HCl re added whilst the solution is hot. After boiling the mixture of ½ hour, the solvent is distilled off, the residue is treated with ammonia and the precipitate is filtered off and recrystallised from methanol. 9-Methyl-7,8,9,10-tetrahydrothieno[3,2-e]pyrido[4,3-b]indole of melting point 189° C. is obtained.

Yield: 3.2 g (66% of theory)

$C_{14}H_{14}N_2S$ (242.348): Calculated: C 69.39%, H 5.82%, N 11.56%, S 13.32%. Found: C 69.43%, H 5.90%, N 11.58%, S 13.30%.

Melting point of the lactate: 185°–189° C.

EXAMPLE 3

9-Benzyl-7,8,9,10-tetrahydrothieno[3,2-e]pyrido[4,3-b]indole lactate

The compound is formed analogously to that described in Example 2, from 9.5 g of 1-benzyl-4-piperidone hydrochloride and 10.0 g of 5-hydrazinobenzothiophene hydrochloride. The unstable base is converted into the lactate. Melting point: 183° C.

Yield: 6.0 g (29% of theory)

$C_{23}H_{24}N_2O_3S$ (408.527): Calculated: C 67.62%, H 5.92 %, N 6.90%, S 7.85%. Found: C 67.48%, H 5.98%, N 6.94%, S 7.76%.

EXAMPLE 4

1-Methyl-7,8,9,10-tetrahydrothieno[3,2-e]pyrido[4,3-b]indole

The compound is formed analogously to that described in Example 2, from 5 g of 5-hydrazino-3-methylbenzothiophene hydrochloride and 5 g of 4-piperidone hydrochloride monohydrate. Melting point: 234° C.

Yield: 4.2 g (74% of theory)

$C_{14}H_{14}N_2S$ (242.348): Calculated: C 69.38%, H 5.82%, N 11.56%, S 13.23%. Found: C 69.47%, H 5.85%, N 11.54%, S 13.17%.

EXAMPLE 5

1,9-Dimethyl-7,8,9,10-tetrahydrothieno[3,2-e]pyrido[4,3-b]indole 15,75 g of 5-hydrazino-3-methylbenzothiophene hydrochloride are suspended in 500 ml of water, a layer of methylene chloride is introduced under the suspension and 10.5 g of 1-methyl-4-piperidone are added at about 0° C. The mixture is then adjusted to pH 9.5 with N NaOH and is stirred for 30 minutes. The organic phase is separated off and washed with saturated NaCl solution, dried and mixed with 500 ml of ethylene glycol and the methylene chloride is distilled off under a vacuum of 12 mm. Some of the glycol is then distilled off under 0.01 mm and at 100° C. and the concentrated solution is heated to 200° C. (bath temperature) in an $N_2$ atmosphere for ½ hour. The crystals which precipitate on cooling the mixture are filtered off, washed and recrystallised from ethyl acetate. Melting point: 224°–227° C.

Yield: 10.2 g (54% of theory)

$C_{15}H_{16}N_2S$ (264.375): Calculated: C 70.27%, H 6.29%, H 10.93%, S 12.51%. Found: C 70.30%, H 6.50%, N 1.93%, S 12.54%.

Melting point of the lactate: 203° C.

Melting point of the hydrochloride: 295° C. (decomposition)

Melting point of the maleate: 216° C. (decomposition)

Melting point of the tartrate: 275° C. (decomposition)

EXAMPLE 6

1-Methyl-9-propyl-7,8,9,10-tetrahydrothieno[3,2-e]pyrido[4,3-b]indole

The compound is formed analogously to that described in Example 5, from 2.15 g of 5-hydrazino-3-methylbenzothiophene hydrochloride and 1.9 g of 1-propyl-4-piperidone. Melting point: 169° C.

Yield: 0.4 g (14% of theory)

$C_{17}H_{20}N_2S$ (284.429): Calculated: C 71.79%, H 7.09%, N 9.58%, S 11.27%. Found: C 71.66%, H 7.18%, N 9.86%, S 11.37%.

Melting point of the lactate: 191°–193° C.

EXAMPLE 7

9-Benzyl-1-methyl-7,8,9,10-tetrahydrothieno[3,2-e]pyrido[4,3-b]indole

The compound is formed analogously to the compound described in Example 5, from 10.1 g of 5-hydrazino-3-methylbenzothiophene and 10 ml of benzyl-4-piperidone. Melting point: 93° C.

Yield: 10.1 g (60% of theory)

$C_{21}H_{20}N_2S$ (332.473): Calculated: C 75.87%, H 6.06%, N 8.43%, S 9.64%. Found: C 75.92%, H 6.21%, N 8.33%, S 9.37%.

EXAMPLE 8

9-(3-Dimethylaminopropyl)-1-methyl-7,8,9,10-tetrahydrothieno[3,2-e]pyrido[4,3-b]indole The compound is formed analogously to that described in Example 5, from 5-hydrazino-3-methylbenzothiophene hydrochloride and 8.5 ml of 1-(3-dimethylaminopropyl)-4-piperidone. Melting point: 184° C.

Yield: 5 g (40% of theory)

$C_{19}H_{25}N_3S$ (363.946): Calculated: C 69.68%, H 7.70%, N 12.83%, S 9.79%. Found: C 69.53%, H 7.69%, N 12.89%, S 9.93%.

Melting point of the hydrochloride: 350° C.

EXAMPLE 9

9-(3-Dimethylaminopropoxycarbonyl)-1-methyl-7,8,9,10-tetrahydrothieno[3,2-e]pyrido[4,3-b]indole Pyridine hydrochloride (obtained from 5 ml of pyridine), 2.1 g of 5-hydrazino-3-methylbenzothiophene hydrochloride and 2.9 g of 1-(3-dimethylaminopropoxycarbonyl)-4-piperidone ethylene-ketal are heated, under $N_2$, first to 100° C. and, after 2 hours, to 120° C. After cooling, the mixture is adjusted to pH 7.5 with NaOH and extracted with methylene chloride, the product phase is washed, dried and concentrated and the residue is chromatographed on $Al_2O_3$ from methylene chloride/methanol (99:1). Melting point: 184° C.

Yield: 0.35 g (9% of theory)

$C_{20}H_{25}N_3O_2S$ (387.51): Calculated: C 61.99%, H 6.50%, N 10.85%. Found: C 62.14%, H 6.64%, N 10.85%.

EXAMPLE 10

9-Methyl-1-phenyl-7,8,9,10-tetrahydrothieno[3,2-e]pyrido[4,3-b]indole

The compound is formed analogously to that described in Example 5, from 14 g of 5-hydrazino-3-phenylbenzothiophene hydrochloride and 6.2 g of 1-methyl-4-piperidone. Melting point: >250° C. (decomposition)

Yield: 7.8 g (49% of theory)

$C_{20}H_{18}N_2S$ (318.45): Calculated: C 75.44%, H 5.70%, N 8.80%, S 10.07%. Found: C 75.31%, H 5.71, N 8.84%, S 9.95%.

EXAMPLE 11

2-Benzyloxycarbonyl-1-methyl-7,8,9,10-tetrahydrothieno[3,2-e]pyrido[4,3-b]indole 1 g of 5-hydrazino-3-methylbenzothiophene-2-carboxylic acid benzyl ester hydrochloride and 1 g of 4-piperidone hydrochloride monohydrate are boiled in 50 ml of isopropanol under $N_2$ for 10 hours. The solvent is then evaporated off, the residue is suspended in water and the aqueous suspension is rendered alkaline with $KHCO_3$ and extracted with ethyl acetate; the extract is washed, dried and evaporated and the residue is recrystallised from isopropanol. Melting point 178° C.

Yield: 0.4 g (37% of theory)

$C_{22}H_{20}N_2O_2S$ (376.484): Calculated: C 70.19%, H 5.35%, N 7.44%, S 8.52%. Found: C 70.31%, H 5.43%, N 7.43%, S 8.55%.

EXAMPLE 12

1,9-Dimethyl-2-benzyloxycarbonyl-7,8,9,10-tetrahydrothieno[3,2-e]pyrido[4,3-b]indole 4.5 g of 5-hydrazino-3-methylbenzothiophene-2-carboxylic acid benzyl ester hydrochloride are suspended in a mixture of HCl and glacial acetic acid; after adding 3 ml of 1-methyl-4-piperidone, the reaction mixture is boiled for 3 hours. The solvent is then evaporated off and the residue is adjusted to pH 7.5, and worked up as described under Example 11. Melting point: 174° C.

Yield: 1.3 g (26% of theory)

$C_{23}H_{22}N_2O_2S$ (390.511):

Calculated: C 70.74%, H 5.68%, N 7.17%, S 8.21%. Found: C 70.71%, H 5.78%, N 7.09%, S 8.11%.

EXAMPLE 13

1-Butyl-9-methyl-7,8,9,10-tetrahydrothieno[3,2-e]pyrido[4,3-b]indole

The compound is formed analogously to that described in Example 5, from 25.6 g of 3-butyl-5-hydrazinobenzothiophene hydrochloride and 13.5 g of 1-methyl-4-piperidone in ethylene glycol, the mixture being heated to 100° C. for 30 minutes and then to 180° C. Melting point: 192°–193° C.

Yield: 18 g (60% of theory)

$C_{18}H_{22}N_2S$ (298.456): Calculated: C 72.44%, H 7.43%; N 9.39%, S 10.74%. Found: C 72.27%, H 7.40%, N 9.51%, S 10.73%.

Melting point of the lactate: melting point 200°–202° C.

Melting point of the malate: melting point 228°–229° C. (salt of malic acid)

EXAMPLE 14

9-sec.-Butyl-7,8,9,10-tetrahydrothieno[3,2-e]pyrido[4,3-b]indole lactate

The compound is formed analogously to that described in Example 12, from 10 g of 5-hydrazinobenzothiophene hydrochloride and 10 g of 1-sec.-butyl-4-piperidone.

The lactate of melting point 170°–171° C. is obtained by adding lactice acid in a solution in acetone.

Yield: 13.5 g (72% of theory)

$C_{20}H_{26}N_2O_3S$ (374.510): Calculated: C 64.14%, H 7.00%, N 7.48%, S 8.56%. Found: C 64.04%, H 6.83%, N 7.51%, S 8.55%.

EXAMPLE 15

9-sec.-butyl-1-methyl-7,8,9,10-tetrahydrothieno[3,2-e]pyrido[4,3-b]indole 11 g of 5-hydrazino-3-methylbenzothiophene hydrochloride and 8.5 g of 1-sec.-butyl-4-piperidone are boiled in 35 ml of isopropanol, and during this procedure isopropanol/HCl are added dropwise. The mixture is then evaporated, the residue is taken up in water and the mixture is rendered alkaline and extracted with methylene chloride. After washing and drying the organic phase, it is evaporated and the residue is recrystallised from cyclohexane. Melting point: 136°–137° C.

Yield: 7 g (46% of theory)

$C_{18}H_{22}N_2S$ (298.46): Calculated: C 72.44%, H 7.43%, N 9.39%, S 10.74%. Found: C 72.37%, H 7.36%, N 9.39%, S 10.63%.

Melting point of the lactate: 171°–175° C.

EXAMPLE 16

5-Isopropyl-7,8,9,10-tetrahydrothieno[3,2-e]pyrido[4,3-b]indole

The compound is formed analogously to that described in Example 15, from 10 g of 5-hydrazinobenzothiophene hydrochloride and 10 g of 1-isopropyl-4-piperidone. Melting point: 197°–199° C.

Yield: 9.5 g (71% of theory)

$C_{16}H_{18}H_2S$ (270.402): Calculated: C 71.07%, H 6.71%, N 10.36%, S 11.86%. Found: C 71.27%, H 6.83%, N 10.61%, S 11.78%.

EXAMPLE 17

9-Isopropyl-1-methyl-7,8,9,10-tetrahydrothieno[3,2-e]pyrido[4,3-b]indole

The compound is formed analogously to that described in Example 15, from 11 g of 5-hydrazino-3-methylbenzothiophene hydrochloride and 10 g of 1-isopropyl-4-piperidone. Melting point: 199°–203° C.

Yield: 8 g (55% of theory)

$C_{17}H_{20}N_2S$ (284.429): Calculated: C 71.79%, H 7.09%, N 9.85%, S 11.27%. Found: C 71.93%, H 7.23%, N 9.80%, S 11.27%.

Melting point of the lactate 203° C.

EXAMPLE 18

1-Butyl-7,8,9,10-tetrahydrothieno[3,2-e]pyrido[4,3-b]indole

The compound is formed analogously to that described in Example 15, from 25.6 g of 3-butyl-5-hydrazinobenzothiophene hydrochloride and 20 g of 4-piperidone hydrochloride monohydrate. Melting point: 224°–225° C.

Yield: 18 g (63% of theory)

$C_{17}H_{20}N_2S$ (284.429): Calculated: C 71.79%, H 7.09%, N 9.85%, S 11.27%. Found: C 71.91%, H 7.14%, N 9.86%, S 11.24%.

Melting point of the lactate: 216°–217° C.

EXAMPLE 19

1-Butyl-9-isopropyl-7,8,9,10-tetrahydrothieno[3,2-e]pyrido[4,3-b]indole

The compound is formed analogously to that described in Example 15, from 25.6 g of 3-butyl-5-hydrazinobenzothiophene hydrochloride and 17 g of 1-isopropyl-4-piperidone. Melting point: 157°–158° C.

Yield: 13 g (40% of theory)

$C_{20}H_{26}N_2S$ (326.510): Calculated: C 73.57%, H 8.03%, N 8.58%, S 9.82%. Found: C 73.67%, H 8.04%, N 8.61%, S 9.72%.

Melting point of the lactate: 183°–185° C.

EXAMPLE 20

9-Propyl-7,8,9,10-tetrahydrothieno[3,2-e]pyrido[4,3-b]indole

This compound is formed analogously to that described in Example 15, from 2 g of 5-hydrazinobenzothiophene hydrochloride and 1.7 g of 1-propyl-4-piperidone. Melting point: 143°–144° C.

Yield: 2.1 g (78% of theory)

$C_{16}H_{18}N_2S$ (270.402): Calculated: C 71.07%; H 6.71%, N 10.36%, S 11.86%. Found: C 71.13%, H 6.72%, N 10.40%, S 11.83%.

EXAMPLE 21

1-Butyl-9-benzyl-7,8,9,10-tetrahydrothieno[3,2-e]pyrido[4,3-b]indole

The compound is formed analogously to that described in Example 5, from 25.6 g of 3-butyl-5-hydrazinobenzothiophene hydrochloride and 23 g of 1-benzyl-4-piperidone. Melting point: 127°–128° C.

Yield: 15 g (40% of theory)

$C_{24}H_{26}N_2S$ (374.554): Calculated: C 76.96%, H 7.00%, N 7.48%, S 8.56%. Found: C 77.06%, H 7.12%, N 7.41%, S 8.57%.

Melting point of the lactate: 138°–139° C.

EXAMPLE 22

1-Phenyl-7,8,9,10-tetrahydrothieno[3,2-e]pyrido[4,3-b]indole 28 g of 5-hydrazino-3-phenylbenzothiophene hydrochloride are dissolved in 300 ml of isopropanol and the solution is combined with 20 g of 4-piperidone hydrochloride monohydrate under an inert gas. After boiling the mixture for 3 hours, the solvent is evaporated off, the residue is taken up in isopropanol and the product is precipitated with the addition of isopropyl ether. The precipitate is filtered off and taken up in water; a layer of methylene chloride is introduced under the solution and the mixture is shaken with NaOH solution. The organic phase is separated off and worked up. Melting point: 228° C. (decomposition)

Yield: 13 g (43% of theory)

$C_{19}H_{16}N_2S$ (304.419): Calculated: C 74.96%, H 5.30%, N 9.20%, S 10.53%. Found: C 74.87%, H 5.13%, N 9.11%, S 10.36%.

EXAMPLE 23

9-sec.-Butyl-1-phenyl-7,8,9,10-tetrahydrothieno[3,2-e]pyrido[4,3-b]indole

The compound is formed analogously to that described in Example 15, from 10 g of 5-hydrazino-3-phenylbenzothiophene hydrochloride and 6.2 g of 1-sec.-butyl-4-piperidone. It is purified on silica gel with methylene chloride/isopropanol/ammonia (10:2:0:05). Melting point: 167°–168° C.

Yield: 9 g (69% of theory)

$C_{23}H_{24}N_2S$ (360.52) Calculated: C 76.62%, H 6.71%, N 7.77%, S 8.89%. Found: C 76.48%, H 6.69%, N 7.82%, S 8.78%.

Melting point of the hydrochloride: 260° C. (decomposition)

EXAMPLE 24

9-Benzyl-1-phenyl-7,8,9,10-tetrahydrothieno[3,2-e]pyrido[4,3-b]indole

The compound is formed from 13.8 g of 3-phenyl-5-hydrazinobenzothiophene hydrochloride and 12 g of 1-benzyl-4-piperidone by a process in which, after boiling the starting materials in isopropanol/HCl under $N_2$ for 1 hour, the mixture is evaporated, the concentrate is taken up in isopropanol, the mixture is rendered alkaline with $NH_4OH$, extracted and evaporated again and the residue is chromatographed on $Al_2O_3$. Melting point: 115°–116° C.

Yield: 7.15 g (36% of theory)

$C_{26}H_{22}N_2S$ (394.54): Calculated: C 79.20%, H 5.62%, N 7.10%, S 8.13%. Found: C 79.25%, H 5.58%, N 7.15%, S 8.01%.

EXAMPLE 25

9-(4-(4-Fluorophenyl)-4-oxobutyl)-1-methyl-7,8,9,10-tetrahydrothieno[3,2-e]pyrido[4,3-b]indole 24 g of 1-methyl-7,8,9,10-tetrahydrothieno[3,2-e]pyrido[4,3-b]indole in 300 ml of dimethylformamide are heated to 80° with 30 g of 4-chloro-1-oxo-1-(4-fluorophenyl)-butane ethylene-ketal under $N_2$. After 4 hours, the solvent is evaporated off and the residue is rendered alkkaline with ammonia and extracted with chloroform. The extract is washed and dried and the solvent is evaporated off. The residue is taken up in methanol/HCl and the mixture is stirred for 2 hours and stored for 12 hours. The hydrochloride which has precipitated is then converted into the base with ammonia/chloroform. Melting pint: 186° C.

Yield: 10 g (25% of theory)

$C_{24}H_{23}FN_2OS$ (406.53): Calculated: C 70.91%, H 5.70%, F 4.67%, N 6.89%, S 7.89%. Found: C 70.73%, H 5.79%, F 4.6%, N 6.82%, S 7.76%.

EXAMPLE 26

9-[4,4-Bis(4-fluorophenyl)butyl]-1-methyl-7,8,9,10-tetrahydrothieno[3,2-e]pyrido[4,3-b]indole 2.4 g of 1-methyl-7,8,9,10-tetrahydrothieno[3,2-e]pyrido[4,3-b]indole are dissolved in 50 ml of dimethylformamide and 10 ml of hexamethylphosphoric acid triamide 4.5 g of 4,4-bis-(4-fluorophenyl)butyl iodide are added and the mixture is warmed to 80° C. under $N_2$ for 5 hours. The solvent is then evaporated off; the residue is taken up in chloroform, the chloroform mixture is washed with water, dried and evaporated, the residue is chromatographed on $Al_2O_3$ with chloroform and the product is recrystallised from isopropanol. Melting point: 158° C.

Yield: 1.9 g (40% of theory)

$C_{30}H_{28}F_2N_2S$ (486.636): Calculated: C 74.04%, H 5.79%, F 7.8%, N 5.75%, S 6.58%. Found: C 73.21%, H 5.40%, F 8.4%, N 5.74% S 6.79%.

EXAMPLE 27

9-(3-Dimethylaminopropyl)-1-methyl-7,8,9,10-tetrahydrothieno[3,2-e]pyrido[4,3-b]indole 10 g of 1-methyl-7,8,9,10-tetrahydrothieno[3,2-e]pyrido[4,3-b]indole, dissolved in 200 ml of dimethylformamide at 90° C., are heated to 90° with a solution of 12 ml of 3-dimethylaminopropyl chloride in 50 ml of dimethylformamide for 3 hours. The reaction mixture is filtered, the filtrate is evaporated and the residue is taken up in chloroform. After washing with water and drying, the organic phase is concentrated, the residue is chromatographed on $SiO_2$ with chloroform/methanol/$NH_4OH$ (7:3:0:1) and the product is recrystallised from isopropanol. Melting point: 184° C.

Yield: 5.1 g (38% of theory)

$C_{19}H_{25}N_3S$ (327.499): Calculated: C 69.68%, H 7.70%, N 12.83%, S 9.79%. Found: C 69.53%, H 7.69%, N 12.89%, S 9.93%.

Melting point of the hydrochloride: >350° C.

EXAMPLE 28

6-Propyl-7,8,9,10-tetrahydrothieno[3,2-e]pyrido[4,3-b]indole maleate 11.5 g of 7,8,9,10-tetrahydrothieno[3,2-e]pyrido[4,3-b]indole are dissolved in 20 ml of dimethylformamide, 2.5 g of an NaH dispersion (50% strength) are added under $N_2$ and the mixture is stirred until the evolution of $H_2$ has ended (about 30 minutes). 4.5 ml of propyl bromide, dissolved in dimethylformamide, are then added dropwise at 0° C. The solvent is evaporated off, the residue is taken up in ether and the ether mixture is washed with N NaOH. After further washing the organic phase with water and drying it, it is evaporated, the base which remains as a yellowish oil is taken up in isopropanol and a solution of 15 g of maleic acid in isopropanol is added. Melting point: 171° C.

Yield: 5 g (25% of theory)

$C_{20}H_{22}N_2O_4S$ (386.48): Calculated: C 62.16%, H 5.74%, N 7.24%. Found: C 62.13%, H 5.50%, N 7.29%.

EXAMPLE 29

9-Methyl-1-phenyl-6-propyl-7,8,9,10-tetrahydrothieno[3,2-e]pyrido[4,3-b]indole

The compound is formed analogously to that described in Example 28, from 4.8 g of 9-methyl-1-phenyl-7,8,9,10-tetrahydrothieno[3,2-e]pyrido[4,3-b]indole, NaH and 1.5 ml of propyl bromide. Melting point: 156° C.

Yield: 2.8 g (52% of theory)

$C_{23}H_{24}N_2S$ (360.527): Calculated: C 76.82%, H 6.71%, N 7.77%, S 8.89%. Found: C 76.68%, H 6.84%, N 7.67%, S 8.87%.

EXAMPLE 30

6,9-Dibenzyl-1-methyl-7,8,9,10-tetrahydrothieno[3,2-e]pyrido[4,3-b]indole

The compound is formed analogously to that described in Example 28, from 3.3 g of 9-benzyl-1-methyl-7,8,9,10-tetrahydrothieno[3,2-e]pyrido[4,3-b]indole and 2 ml of benzyl bromide in 50 ml of hexamethylphosphoric acid triamide in the presence of NaH. Melting point: 206° C.

Yield: 2 g (48% of theory)

EXAMPLE 31

6-(3-Dimethylaminopropyl)-1,9-dimethyl-7,8,9,10-tetrahydrothieno[3,2-e]pyrido[4,3-b]indole dihydrochloride 4.0 g of 1,9-dimethyl-7,8,9,10-tetrahydrothieno[3,2-e]pyrido[4,3-b]indole are dissolved in 60 ml of dimethylformamide, 0.78 g of a 50% strength dispersion of NaH is added, whilst stirring, and, after 1 hour, 2.4 g of 3-dimethylaminopropyl chloride are added. After leaving the mixture is stand for 15 hours, the solvent is evaporated off, the residue is taken up in ethyl acetate, the ethyl acetate mixture is washed and dried and the product is purified on SiO$_2$ with chloroform/methanol (1:1). The dihydrochloride is then prepared with isopropyl alcohol/HCl. Melting point: 263° C.

Yield: 3 g (46% of theory)

C$_{20}$H$_{27}$N$_3$S.2HCl (414.456): Calculated: C 57.96%, H 7.05%, N 10.14%, S 7.74%, Cl 17.11%. Found: C 58.35%, H 7.35%, N 9.69%, S 7.52%, Cl 16.69%.

EXAMPLE 32

9-Benzyl-6-(3-dimethylaminopropyl)-1-methyl-7,8,9,10-tetrahydrothieno[3,2-e]pyrido[4,3-b]indole The compound is formed from 6.6 g of 9-benzyl-1-methyl-7,8,9,10-tetrahydrothieno[3,2-e]pyrido[4,3-b]indole, 1.0 g of a 50% strength dispersion of NaH and 3 ml of 3-dimethylaminopropylchloride in 50 ml of hexamethylphosphoric acid triamide at 20° C. in the course of 2 hours. The mixture is worked up in the customary manner. The base obtained melts at 109° C.

Yield: 6.0 g (72% of theory)

C$_{26}$H$_{31}$N$_3$S (417.624): Calculated: C 74.47%, H 7.48%, N 10.06%, S 7.68%. Found: C 74.81%, H 7.47%, N 10.19%, S 7.80%.

Melting point of the dihydrochloride: 238° C.

EXAMPLE 33

6-(3-Dimethylaminopropyl)-1-methyl-7,8,9,10-tetrahydrothieno[3,2-e]pyrido[4,3-b]indole The compound is formed analogously to that described in Example 31, from 4.8 g of 1-methyl-7,8,9,10-tetrahydrothieno[3,2-e]pyrido[4,3-b]indole, 1.0 g of a dispersion of NaH and 2.4 ml of 3-dimethylaminopropyl chloride in dimethylformamide. Melting point: 92° C.

Yield: 1.4 g (22% of theory)

C$_{19}$H$_{25}$N$_3$S (327.499): Calculated: C 69.68%, H 7.69%, N 12.83%, S 9.79%. Found: C 69.65%, H 7.79%, N 12.72%, S 9.91%.

Melting point of the dihydrochloride: 193° C. (decomposition).

EXAMPLE 34

6,9-Bis-(3-dimethylaminopropyl)-1-methyl-7,8,9,10-tetrahydrothieno[3,2-e]pyrido[4,3-b]indole trimaleate The compound is formed analogously to that described in Example 31, from 5 g of 9-(3-dimethylaminopropyl)-1-methyl-7,8,9,10-tetrahydrothieno[3,2-e]pyrido[4,3-b]indole, NaH and 3-dimethylaminopropyl chloride indimethylformamide, the product subsequently being converted into the maleate. Melting point: 174° C.

Yield: 7.9 g (68% of theory)

C$_{24}$H$_{36}$N$_4$5.3C$_4$H$_4$O$_4$ (760.878): Calculated: C 56.83%, H 6.39%, N 7.36%, S 4.21%. Found: C 57.51%, H 6.30%, N 7.38%, S 3.28%.

EXAMPLE 35

1,9-Dimethyl-7,8,9,10-tetrahydrothieno[3,2-e]pyrido[4,3-b]indole N$_{(9)}$-methiodide 5 g of 1,9-dimethyl-7,8,9,10-tetrahydrothieno[3,2-e]pyrido[4,3-b]indole are dissolved in 200 ml of ethanol, and 10 ml of methyl iodide are added. After leaving the mixture to stand for a prolonged period, the end product crystallises out. Melting point: 280°-285° C. (decomposition)

Yield: 6.5 g (84% of theory).

C$_6$H$_{19}$IN$_2$S (398.320): Calculated: C 48.25%, H 4.81%, N 7.03%. Found: C 48.39%, H 4.87%, N 6.95%.

EXAMPLE 36

9-Methyl-1-ethyl-7,8,9,10-tetrahydrothieno[3,2-e]pyrido[4,3-b]indole 6.0 g of 3-ethyl-5-hydrazinobenzothiophene hydrochloride are suspended in 100 ml of water, a layer of methylene chloride is introduced under the suspension and sodium bicarbonate is added, whilst stirring. After 15 minutes, the organic phase is separated off, washed with water, dried over sodium sulphate and filtered and the filtrate is evaporated to dryness. The base is taken up in 60 ml of ethylene glycol, 4.0 g of 1-methyl-4-piperidone are added and, after stirring at room temperature for 1 hour, the mixture is heated at 165° C. for 3 hours. It is allowed to cool, 60 ml of methanol are added to the still warm solution and the product is allowed to crystallise out. The crude product is purified by column chromatography on silica gel with chloroform/methanol (8:2). Melting point: 181°-182° C.

Yield: 4.0 g (57% of theory)

C$_{16}$H$_{18}$N$_2$S (270.402): Calculated: C 71.07%, H 6.71%, N 10.36%, S 11.85%. Found: C 70.95%, H 6.72%, N 10.29%, S 11.59.

EXAMPLE 37

1,9-Diethyl-7,8,9,10-tetrahydrothieno[3,2-e]pyrido[4,3-b]indole

The compound is formed analogously to that described in Example 36, from 8.0 g of 3-ethyl-5-hydrazinobenzothiophene hydrochloride and 6.0 g of 1-ethyl-4-piperidone, by cyclisation under the influence of heat at 165°-170° C. in ethylene glycol for 3 hours.

The cold reaction mixture is diluted with water and than extracted twice by shaking with chloroform. The crude product obtained after drying the mixture and evaporating off the solvent is purified by chromatography on silica gel with chloroform/methanol (8:2). The colourless substance melts at 158°-159° C.

Yield: 5.4 g (55% of theory)

C$_{17}$H$_{20}$N$_2$S (284.426): Calculated: C 71.79%, H 7.08%, N 9.85%. Found: C 71.79%, H 7.05%, N 9.67%.

EXAMPLE 38

1-Ethyl-9-isopropyl-7,8,9,10-tetrahydrotheino[3,2-e]pyrido[4,3-b]indole

The compound is formed analogous to that described in Example 37, from 8.0 g of 3-ethyl-5-hydrazinobenzothiophene hydrochloride and 7.0 g of 1-isopropyl-4-piperidone by heating the starting materials in ethylene glycol for 3 hours. Melting point: 183° C.

Yield: 4.0 g (38% of theory)

C$_{18}$H$_{22}$H$_2$S (298.45): Calculated: C 72.44%, H 7.43%, N 9.38%. Found: C 72.42%, H 7.31%, N 9.39%.

EXAMPLE 39

9-Allyl-1-ethyl-7,8,9,10-tetrahydrothieno[3,2-e]pyrido[4,3-b[indole

The compound is formed analogously to that described in Example 37, from 9.0 g of 3-ethyl-5-hydrazinobenzothiophene hydrochloride and 8.0 g of 1-allyl-4-piperidone by heating the starting materials in ethylene glycol for 3 hours. Melting point: 143°-144° C.

Yield: 5.0 g (43% of theory)

C$_{18}$H$_{20}$N$_2$S (296.436): Calculated: C 72.93%, H 6.80%, N 9.45%. Found: C 72.89%, H 6.71%, N 9.43%.

EXAMPLE 40

1-isopentyl-9-methyl-7,8,9,10-tetrahydrothieno[3,2-e]pyrido[4,3-b]indole 27.0 g of 5-hydrazino-3-isopentylbenzothiophene hydrochloride are suspended in 250 ml of diethyl ether, and 50 ml of 2 N NaOH are added, whilst stirring. After 10 minutes, the phases are separated, the ether solution is washed with water, dried over sodium sulphate and filtered and the filtrate is evaporated. 200 ml of ethylene glycol and 14.8 ml of 1-methyl-4-piperidone are added to the residue and the mixture is heated to 180° C. for 1 hour. The crystalline product obtained after cooling the mixture is recrystallised from isopropanol. Melting point: 184°–185° C.

Yield: 15.0 g (48% of theory)

C$_{19}$H$_{24}$N$_2$S (312.483): Calculated: C 73.03%, H 7.77%, N 8.96%, S 10.26%. Found: C 72.88%, H 7.72%, N 9.04%, S 10.36%.

Melting point of the lactate: 195°–196° C.

Melting point of the dihydrogen phosphate: 261°–263° C.

EXAMPLE 41

9-Ethyl-1-phenyl-7,8,9,10-tetrahydrothieno[3,2-e]pyrido[4,3-b]indole 13.8 g of 5-hydrazino-3-phenylbenzothiophene hydrochloride and 6.7 g of 1-ethyl-4-piperidone are stirred in 60 ml of absolute isopropanol for 1 hour, the same amount of isopropanol containing hydrogen chloride is then added and the mixture is boiled under reflux for 4 hours. After evaporating off the solvent, the residue is treated with N NaOH and the base is extracted with methylene chloride. The substance, recrystallised from toluene, melts at 233° C., with decomposition.

Yield: 8.2 g (49% of theory)

C$_{21}$H$_{20}$N$_2$S (332.5): Calculated: C 75.87%; H 6.06%. Found: C 75.84%, H 6.18%.

Melting point of the lactate: 163°–164° C.

EXAMPLE 42

9-Propyl-1-phenyl-7,8,9,10-tetrahydrothieno[3,2-e]pyrido[4,3-b]indole

The compound is formed analogously to that described in Example 40, from 13.8 g of 5-hydrazino-3-phenylbenzothiophene hydrochloride and 7.5 g of 1-propyl-4-piperidone by boiling the starting materials in 120 ml of isopropanol containing hydrogen chloride for 4 hours. Melting point: 187°–188° C.

Yield: 7.0 g (40% of theory)

C$_{22}$H$_{22}$N$_2$S (346.5): Calculated: C 76.26%, H 6.40%, N 8.08%, S 9.25%. Found: C 75.52%, H 6.37%, N 8.11%, S 9.21%.

Melting point of the lactate: 185° C.

EXAMPLE 43

9-Isopropyl-1-phenyl-7,8,9,10-tetrahydrothieno[3,2-e]pyrido[4,3-b]indole

The compound is formed analogously to that described in Example 40, from 13.8 g of 5-hydrazino-3-phenylbenzothiophene hydrochloride and 7.5 g of 1-isopropyl-4-piperidone by boiling the starting materials in 120 ml of isopropanol containing hydrogen chloride for 4 hours. Melting point: 204° C.

Yield: 6.0 g (35% of theory)

C$_{22}$H$_{22}$N$_2$S (346.5): Calculated: C 76.26%, H 6.40%, N 8.06%, S 9.25%. Found: C 75.55%, H 6.42%, N 8.08%, S 9.21%.

Melting point of the lactate: 205° C.

EXAMPLE 44

9-Phenethyl-1-phenyl-7,8,9,10-tetrahydrothieno[3,2-e]pyrido[4,3-b]indole 28.0 g of 5-hydrazino-3-phenylbenzothiophene hydrochloride are allowed to react with 21.0 g of N-(2-phenethyl)-4-piperidone in 500 ml of isopropanol at room temperature for 2 hours. After filtering off the crystall sludge, this is suspended in 150 ml of N NaOH and the suspension is extracted with methylene chloride. The organic phase is washed with water until neutral and evaporated, the oily residue is taken up in 400 ml of ethylene glycol and the mixture is heated to 190° C. for 30 minutes. The substance which has crystallised out after cooling is filtered off and recrystallised from toluene. Melting point: 220°–221° C.

Yield: 13.0 g (32% of theory)

C$_{27}$H$_{24}$N$_2$S (408.60): Calculated: C 79.37%, H 5.9%, N 7.77%, S 7.84%. Found: C 79.49%, H 5.91%, H 7.67%, S 7.75%.

The active compounds listed in Table 1 are prepared analogously to Examples 5, 12 and 15.

The compounds summarised in Table 2 are synthesised analogously to Examples 26 to 28.

TABLE 1

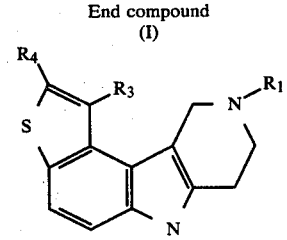

End compound (I)

Starting compound (II)

Starting compound (III)

| Example | R$_3$ | R$_4$ | R$_2$ | Melting point (°C.) | | Yield of base in % of theory | Notes<br>Reaction medium<br>Reaction time<br>Temperature |
|---|---|---|---|---|---|---|---|
| 45 | —CH$_2$CH$_2$CH$_2$CH$_3$ | H | —CH$_2$CH$_3$ | 140–141<br>188–189 | (base)<br>(lactate) | 49 | Ethylene glycol; 140 minutes; 185° C. |
| 46 | —CH$_2$CH$_2$CH$_2$CH$_3$ | H | —CH$_2$CH$_2$CH$_3$ | 126–127 | (base) | 44 | Ethylene glycol; 40 |

TABLE 1-continued

End compound (I)

Starting compound (II) / Starting compound (III)

| Example | R₃ | R₄ | R₂ | Melting point (°C.) | | Yield of base in % of theory | Notes / Reaction medium / Reaction time / Temperature |
|---|---|---|---|---|---|---|---|
| 47 | —CH₂CH₃ | H | —H | 187 | (lactate) | 38 | Glacial acetic acid; |
|  |  |  |  | 215–216 | (base) |  | 150 minutes; 185° C. |
|  |  |  |  | 206 | (lactate) |  |  |
| 48 | —CH₂CH₂CH₂CH₃ | H | —CH₂CH(CH₃)₂ | 108 | (base) | 32 | Ethylene glycol; 40 minutes; 185° C. |
|  |  |  |  | 170–171 | (lactate) |  |  |
| 49 | —CH₂CH₂CH₂CH₃ | H | —CH₂CH=CH₂ | 128 | (base) | 48 | Ethylene glycol; 45 minutes; 185° C. |
|  |  |  |  | 140 | (lactate) |  |  |
| 50 | —CH₂CH₂CH(CH₃)₂ | H | —H | 182 | (base) | 60 | Isopropanol/HCl; 120 minutes; reflux |
|  |  |  |  | 190–191 | (lactate) |  |  |
| 51 | —CH₂CH₂CH(CH₃)₂ | H | —CH₂CH=CH₂ | 131 | (base) | 53 | Isopropanol/HCl; 90 minutes; reflux |
|  |  |  |  | 156–158 | (lactate) | 53 |  |
| 52 | —CH₂CH₂CH(CH₃)₂ | H | Cyclohexyl-C₆H₁₁ | 165 | (base) | 60 | Isopropanol/HCl; 60 minutes; reflux |
|  |  |  |  | 173–175 | (lactate) |  |  |
| 53 | —CH₂CH₃ | H | Phenyl-C₆H₅ | 181–182 | (base) | 49 | Glacial acetic acid; 60 minutes; 70° C. |
| 54 | —CH₂CH₂C₆H₅ | H | —CH₃ | 181 | (lactate) | 45 | Isopropanol/HCl; 180 minutes; reflux |
| 55 | —CH₂CH₂C₆H₅ | H | —CH₂CH₂CH₃ | 171 | (lactate) | 52 | Isopropanol/HCl; 150 minutes; reflux |
| 56 | —CH₃ | H | —CH₂CH₃ | 201 | (base) | 50 | Isopropanol/HCl; 30 minutes; reflux |
|  |  |  |  | 201 | (lactate) |  |  |

TABLE 2

End compound (I)

Starting compound

| Example | R₂ | R₃ | R₄ | R₁ | Melting point (0° C.) | Yield of base in % of theory | Notes / Reaction medium / Alkylating agent / Reaction time / Temperature |
|---|---|---|---|---|---|---|---|
| 57 | —CH₃ | ⟨phenyl⟩ | H | —CH₂CH₂CH(CH₃)₂ | 147 (base) | 73 | Dimethylformamide/ NaH; R₁—Br; 6 hours; 20° C. |
| 58 | —CH₃ | —CH₂CH₂CH(CH₃)₂ | H | —CH₂CH₂—O—CH₃ | 127–128 (base) | 61 | Hexamethylphosphoric acid triamide/NaH; R₁—Cl; 16 hours; 20° C. |
| 59 | —CH₃ | —CH₂CH₂CH(CH₃)₂ | H | —CH₂CH₂CH₂N(CH₃)₂ | 238–240 (decomposition) | 55 | Hexamethylphosphoric acid triamide/NaH; R₁—Cl; 32 hours; 20° C. |
| 60 | H | —CH₃ | H | R₁ and R₂ = —CH₂—⟨cyclohexyl-H⟩ | 244 (hydrochloride) | 23 | Dimethylformamide/ NaH; R₁—Br; 2 hours; 80° C. |

TABLE 2-continued

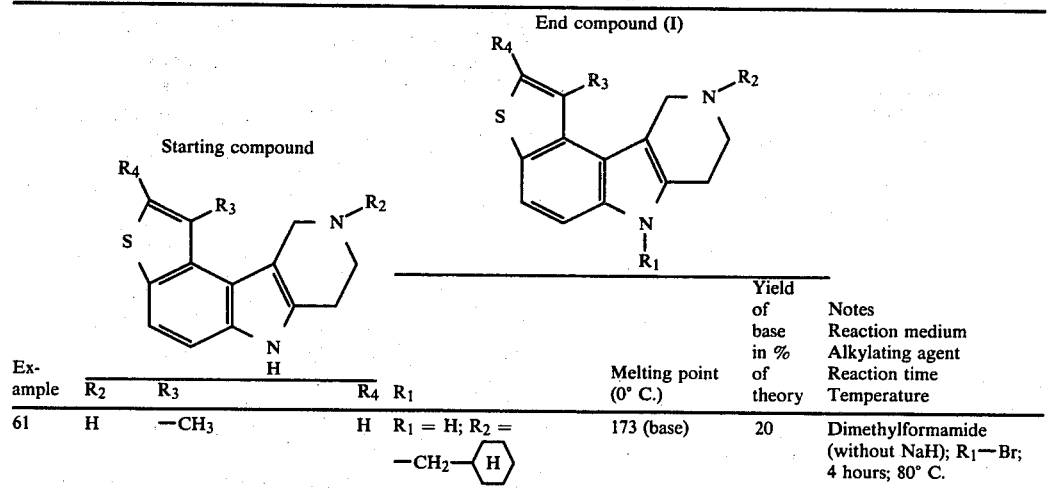

| Example | R2 | R3 | R4 | R1 | Melting point (0° C.) | Yield of base in % of theory | Notes Reaction medium Alkylating agent Reaction time Temperature |
|---|---|---|---|---|---|---|---|
| 61 | H | —CH3 | H | R1 = H; R2 = —CH2—⟨H⟩ | 173 (base) | 20 | Dimethylformamide (without NaH); R1—Br; 4 hours; 80° C. |

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A 7,8,9,10-tetrahydrothieno pyrido indoles of the formula

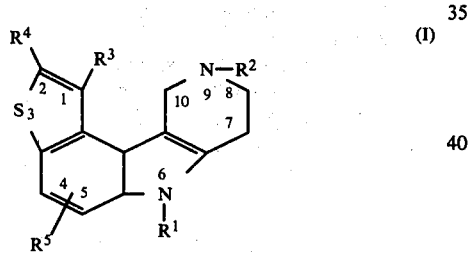

a $C_1$–$C_4$-alkyl quaternary ammonium halide or hydroxyalkyl halide thereof, or an acid or base addition salt thereof, in which $R^1$ $R^2$ and $R^3$ are identical or different and each denotes a hydrogen atom, a straight-chain or branched alkyl, alkenyl or alkinyl group each having up to 12 carbon atoms and in which one $CH_2$ group is optionally replaced by an oxygen atom or an unsubstituted or $C_1$–$C_4$-alkyl-substituted nitrogen atom and in which one hydrogen atom is optionally replaced by halogen or hydroxy, denotes a mono-or bi-cyclic carbocyclic aryl or ar-$C_1$–$C_2$-alkyl group, in which the aryl ring is optionally substituted by 1 or 2 lower alkyl or alkoxy, halogen, hydroxyl groups or one trifluoromethyl group, denotes a $C_3$–$C_6$-cycloalkyl or $C_3$–$C_6$-cycloalkyl-$C_1$–$C_3$-alkyl group, in which the cycloalkyl radical is optionally substituted by lower alkyl or halogen, denotes a mono-or bi-cyclic carbocyclic aryloxyalkyl, in which the aryl radical is optionally substituted by 1 or 2 lower alkyl or alkoxy, hydroxyl or halogen, denotes a mono-or bi-cyclic carbocyclic aroylalkyl group, in which the aroyl group is optionally substituted by 1 or 2 lower alkyl or alkoxy or by halogen atoms, denotes a heterocyclic or heterocycloalkyl group which is a member selected from the group consisting of piperidino-ethyl pyrrolidinopropyl, morpholinopropyl, thiomorpholinopropyl, morpholinobutyl, morpholinopentyl, piperazinoethyl, piperazinopropyl, piperazinobutyl and 4-piperidyl, which is optionally substituted by a lower alkyl group, an unsubstituted or substituted mono- or bi-cyclic carbocyclic aryl or aralkyl group in which the substituents on the aryl portion are halogen, methyl or methoxy, denote a carboxyl or optionally esterified carboxyl group, the ester radicals being straight-chain or branched $C_1$–$C_6$ alkyl group in which one hydrogen atom is optionally replaced by phenyl, hydroxyl, $C_1$–$C_{12}$-alkoxy, amino or lower $C_1$–$C_{12}$-alkylamino or di-$C_1$–$C_{12}$-alkylamino, denotes a carboxamide grouping, in which the nitrogen atom is optionally substituted by lower alkyl groups, $R^4$ denotes a hydrogen atom, a lower alkyl group, an aryl group which is unsubstituted or substituted by one or two methyl or ethyl groups, halogen atoms or methoxy groups, or $R^4$ is a carboxyl group, a carboxyl group esterified by a lower alkyl or aralkyl, or an optionally substituted carboxamide group selected from the group consisting of an aminocarbonyl, methyl- or dimethyl-amino-carbonyl, ethyl- or diethyl-aminocarbonyl, phenylaminocarbonyl, benzylaminocarbonyl or cycloalkylaminocarbonyl group, the cycloalkyl ring containing 3 to 6 ring members and $R^5$ denotes a hydrogen or halogen atom or a lower alkyl group or an alkoxy group.

2. A compound according to claim 1, in which $R^1$ denotes a hydrogen atom or a straight-chain or branched alkyl group with 1 to 4 carbon atoms which is optionally substituted by alkoxy with 1 or 2 carbon atoms or by alkylamino or dialkylamino with in each case 1 or 2 carbon atoms per alkyl radical, denotes a mono- or bi-cyclic carbocyclic aryl-$C_1$–$C_2$-alkyl group, the aryl radical thereof optionally being substituted by halogen or denotes a mono- or bi-cyclic carbocyclic aryl radical, the aryl radical optionally being substituted by alkyl or alkoxy with 1 or 2 carbon atoms or optionally being substituted by halogen, hydroxyl or trifluoromethyl, $R^2$ denotes a hydrogen atom or a straight-chain or branched or cyclic alkyl group with up to 6 carbon atoms, this alkyl group optionally being substituted by alkoxy with 1 or 2 carbon atoms or by alkylamino or dialkylamino radicals with in each case 1 or 2 carbon atoms in the alkyl part, denotes a mono- or bi-cyclic carbocyclic aryl radical, this aryl radical optionally being substituted by alkyl with in each case 1 or 2 carbon atoms or by alkoxy with 1 or 2 carbon atoms or by halogen or trifluoromethyl, denotes a mono- or bi-cyclic carbocyclic aryl-$C_1$-$C_2$-alkyl radical, the aryl ring thereof optionally being substituted by halogen, denotes an alkenyl radical with up to 4 carbon atoms, denotes an alkoxycarbonyl radical with up to 4 carbon atoms in the alkoxy radical, this alkoxy radical optionally being substituted by dialkylamino with in each case 1 or 2 carbon atoms in the alkyl group, denotes a phenyloxoalkyl radical, the alkyl radical thereof containing up to 4 carbon atoms and the phenyl radical thereof optionally being substituted by halogen, or denotes a biphenylalkyl radical with 1 to 4 carbon atoms in the alkyl radical, the phenyl radical thereof optionally being substituted by halogen, $R^3$ denotes a hydrogen atom or a straight-chain or branched alkyl with 1 to 6 carbon atoms is optionally substituted by halogen, or denotes a phenyl radical which is optionally substituted by halogen or trifluoromethyl, $R^4$ denotes a hydrogen atom, an alkyl group with 1 to 4 carbon atoms, or a benzyloxycarbonyl group, and $R^5$ denotes a hydrogen atom.

3. A compound according to claim 2 in which the substituent on the aralkyl or aryl radical on $R^1$ and/or on the phenyl ring of the aralkyl, phenyloxoalkyl or biphenylalkyl radical of $R^2$ and/or on the alkyl radical of $R^3$ is a fluorine or chlorine atom.

4. A compound according to claim 2 in which $R^1$ denotes a benzyl or phenyl radical.

5. A compound according to claim 2 or 4 in which $R^2$ denotes a phenyl, benzyl, phenylethyl, 4-(4-fluorophenyl)-4-oxobutyl or 4,4-bis-(4-fluorophenyl)-butyl radical.

6. A compound according to claim 2 in which $R^4$ denotes an alkyl group with 1 or 2 carbon atoms.

7. A compound according to claim 1, in which
$R^1$ denotes a hydrogen atom or a straight-chain or branched alkyl group with 1 to 4 carbon atoms, which is optionally substituted by alkoxy with 1 or 2 carbon atoms, or a phenyl radical,
$R^2$ denotes a hydrogen atom, a straight-chain or branched or cyclic alkyl group with up to 6 carbon atoms, a phenyl radical or a benzyl radical,
$R^3$ denotes a hydrogen atom, an alkyl group with 1 or 2 carbon atoms or an aralkyl radical,
$R^4$ denotes a hydrogen atom or an alkyl group with 1 or 2 carbon atoms and
$R^5$ denotes a hydrogen atom.

8. A compound according to claim 2 or 3 in which $R^1$, $R^2$, $R^3$, $R^4$ and $R^5$ have the same meanings as in claim 2 or 3 with the proviso that neither $R^1$ nor $R^2$ denotes the optionally substituted aryl radical.

9. A compound according to claim 2 which is 1-9-Dimethyl-7,8,9,10-tetrahydrothieno[3,2-e]pyrido[4,3-b]indole.

10. A compound according to claim 2 which is 9-Methyl-1-ethyl-7,8,9,10-tetrahydrothieno[3,2-e]pyrido[4,3-b]indole.

11. A compound according to claim 2 which is 1,9-Diethyl-7,8,9,10-tetrahydrothieno[3,2-e]pyrido[4,3-b]indole.

12. A compound according to claim 2 which is 1-methyl-9-ethyl-7,8,9,10-tetrahydrothieno[3,2-e]pyrido[4,3-b]indole.

13. A pharmaceutical composition containing as an active ingredient an anti-depressively effective amount of a compound according to claim 1 in admixture with a solid, liquid or liquefied pharmaceutically acceptable diluent.

14. A pharmaceutical composition of claim 13 in the form of a sterile or physiologically isotonic aqueous solution.

15. A compound according to claim 13 or 14 containing from 0.5 to 95% by weight of the said active ingredient.

16. A medicament in dosage unit form comprising an anti-depressively effective amount of a compound according to claim 1 together with an inert pharmaceutical carrier.

17. A medicament of claim 16 in the form of tablets, pills, dragees, capsules, ampoules, or suppositories.

18. A method of combating depression in warm-blooded animals which comprises administering to the animals an anti-depressively effective amount of an active compound according to claim 1 either alone or in admixture with a diluent or in the form of a medicament.

19. A method according to claim 18 in which the active compound is administered in an amount of 0.1 to 10 mg per kg body weight per day.

20. A method according to claim 18 or 19 in which the active compound is administered orally or intravenously.

21. A pharmaceutical composition of claim 13 in which the active ingredient is 1-9-Dimethyl-7,8,9,10-tetrahydrothieno[3,2-e]pyrido[4,3-b]indole.

22. A pharmaceutical composition of claim 13 in which the active ingredient is 9-Methyl-1-ethyl-7,8,9,10-tetrahydrothieno[3,2-e]pyrido[4,3-b]indole.

23. A pharmaceutical composition of claim 13 in which the active ingredient is 1,9-Diethyl-7,8,9,10-tetrahydrothieno[3,2-e]pyrido[4,3-b]indole.

24. A pharmaceutical composition of claim 13 in which the active ingredient is 1-methyl-9-ethyl-7,8,9,10-tetrahydrothieno[3,2-e]pyrido[4,3-b]indole.

* * * * *

UNITED STATES PATENT AND TRADEMARK OFFICE
CERTIFICATE OF CORRECTION

PATENT NO. : 4,410,536
DATED : October 18, 1983
INVENTOR(S) : Karl-Heinz Boltze et al It is certified that error appears in the above-identified patent and that said Letters Patent is hereby corrected as shown below:

Col. 1, line 15     Correct beginning of formula as follows:

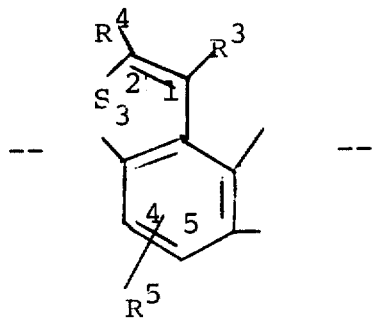

| | |
|---|---|
| Col. 2, line 67 | Delete "an" and insert --as-- |
| Col. 4, line 45 | Delete "A$_{c2}$D" and insert --A$_{c2}$O-- |
| Col. 3, line 67 | Delete "S" before "Sauter" and insert --F-- |
| Col. 7, line 52 | Delete "dimathyl" and insert --dimethyl-- |
| Col. 12, line 11 | Delete "glycoles" and insert --glycols-- |
| Col. 13, line 30 | Delete "effectie" and insert --effective-- |
| Col. 13, line 62 | Delete "S$_2$Cl$_2$" and insert --SnCl$_2$-- |
| Col. 14, line 52 | Delete "afe" and insert --has-- |
| Col. 15, line 36 | Delete "3.2" and insert --3,2-- |
| Col. 15, line 53 | Delete "210°220°" and insert --210°-220°-- |
| Col. 15, line 64 | Delete "re" and insert --are-- |
| Col. 17, line 36 | Delete "363.946" and insert --363.964-- |

UNITED STATES PATENT AND TRADEMARK OFFICE
CERTIFICATE OF CORRECTION

PATENT NO. : 4,410,536  Page 2 of 2

DATED : October 18, 1983

INVENTOR(S) : Karl-Heinz Boltze et al

It is certified that error appears in the above-identified patent and that said Letters Patent is hereby corrected as shown below:

| | |
|---|---|
| Col. 19, line 25 | Delete "5" and insert --9-- |
| Col. 21, line 30 | Delete "alkkaline" and insert --alkaline-- |
| Col. 24, line 2 | Delete "$C_6H_{19}IN_2S$" and insert --$C_{16}H_{19}IN_2S$-- |
| Col. 24, line 48 | Delete "tetrahydrotheino" and insert --tetrahydrothieno-- |
| Col. 24, line 50 | Delete "analogous" and insert --analogously-- |
| Col. 26, line 33 | Delete "crystall" and insert --crystal-- |
| Col. 26, line 42 | Delete "5.9" and insert --5.92-- |

Signed and Sealed this

Tenth Day of July 1984

[SEAL]

Attest:

GERALD J. MOSSINGHOFF

Attesting Officer

Commissioner of Patents and Trademarks